United States Patent [19]

Haviv et al.

[11] Patent Number: 4,503,056
[45] Date of Patent: Mar. 5, 1985

[54] 1-(PYRIDAZINYL)PYRAZOLINE DERIVATIVES

[75] Inventors: Fortuna Haviv, Deerfield; Roland L. Walters, Des Plaines, both of Ill.

[73] Assignee: Abbott Laboratories, North Chicago, Ill.

[21] Appl. No.: 354,118

[22] Filed: Mar. 2, 1982

[51] Int. Cl.³ ............... C07D 231/06; C07D 237/06; A61K 31/50
[52] U.S. Cl. .................... 514/252; 544/238; 544/239; 548/379
[58] Field of Search ............... 544/238, 239; 548/379; 424/250

[56] References Cited

U.S. PATENT DOCUMENTS

| | | | |
|---|---|---|---|
| 3,657,243 | 4/1972 | Quintilla | 544/238 |
| 4,224,325 | 9/1980 | Szilagyi | 544/238 |
| 4,239,901 | 12/1980 | Rainer | 548/379 |
| 4,251,658 | 2/1981 | Szilagyi | 544/238 |

FOREIGN PATENT DOCUMENTS 2831072 5/1979 Fed. Rep. of Germany ...... 544/238

OTHER PUBLICATIONS

Burger, Alfred, *Medicinal Chemistry* IVth, pp. 1224–1225.
Matsuura et al., *Chem. Abst.* 87: 68353u.
Burger, *Medicinal Chemistry*, Wiley Interscience, New York, (1970).
Szilagyi et al., "3(Pyrazol-1'-yl)Pyridazine Derivatives", *Chem. Abst.* 90: 152221.
Szilagyi et al., "3(Pyrazol-1'-yl)Pyridazine", *Chem. Abst.* 91: 107995.
Robertson et al., *Medical Clinics of North America*, vol. 65, No. 4, W. B. Saunders, Philadelphia, (1981), pp. 70–72.

Primary Examiner—Donald G. Daus
Assistant Examiner—G. Hendricks
Attorney, Agent, or Firm—Steven F. Weinstock; Martin L. Katz; Gildo E. Fato

[57] ABSTRACT

Described are compounds of the formula

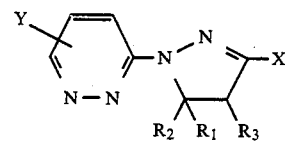

wherein $R_1$, $R_2$ and $R_3$ independently of one another denote hydrogen or loweralkyl, X is hydroxy or amino, and Y is hydrogen, loweralkyl, loweralkoxy, benzyl or

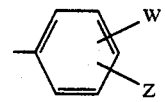

wherein W and Z independently of one another denote hydrogen, halo, loweralkyl, loweralkoxy, trifluoromethyl, acetamido, cyano, diloweralkylamino, phenoxy and loweralkylmercapto, and pharmaceutically acceptable salts thereof.

The compounds are effective as anti-inflammatory agents.

18 Claims, No Drawings

1-(PYRIDAZINYL)PYRAZOLINE DERIVATIVES

BACKGROUND OF THE INVENTION

The present invention provides compositions for the treatment of rheumatoid arthritis, type III hypersensitivity diseases, diseases in which polymorphonuclear leukocyte accumulation contributes to the pathology, and other inflammatory conditions. An anti-inflammatory composition in dosage unit form is described.

SUMMARY OF THE INVENTION

The present invention is directed to compounds of the formula

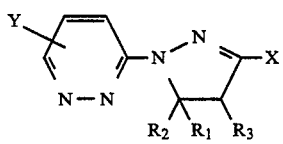

wherein $R_1$, $R_2$ and $R_3$ independently of one another denote hydrogen or loweralkyl, X is hydroxy or amino, and Y is hydrogen, loweralkyl, loweralkoxy, benzyl or

wherein W and Z independently of one another denote hydrogen, halo, loweralkyl, loweralkoxy, trifluoromethyl, acetamido, cyano, diloweralkylamino, phenoxy and loweralkylmercapto, and pharmaceutically acceptable salts thereof.

The terms "loweralkyl" and "loweralkoxy" as used herein refer to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "halo" as used herein refers to chloro, bromo, fluoro and iodo.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg/kg per day per patient are useful, with the total dose of up to 0.5 to 5.0 gm per day being a suitable range for large animals, including humans.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

Depending on the specific compound to be made, the compounds of Formula I can be prepared by the reaction of the appropriate hydrazino pyridazine with acrylonitrile in alcohol or tetrahydrofuran in the presence of base such as sodium ethoxide, sodium hydroxide, chlorine, etc. The obtained product is generally purified by crystallization.

In order to illustrate the manner in which the above compounds may be prepared and the properties of the compounds, reference is made to the following examples, which, however, are not meant to limit or restrict the scope of the invention in any respect.

EXAMPLE 1

1-[6'-Phenylpyridazin-3'-yl]-3-aminopyrazol-2-ene

To a solution of sodium metal (0.125 g) in absolute ethanol (35 ml) was added 6-phenyl-3-hydrazinopyridazine (3.5147 g) and acrylonitrile (1.55 ml). The mixture was heated under reflux under a nitrogen atmosphere with stirring for 6 hours. The mixture was cooled in an ice bath. The crude product was filtered and crystallized from anhydrous ethanol to give 1-[6'-phenyl-pyridazin-3'-yl]-3-aminopyrazol-2-ene, m.p. 233°–235° C.

EXAMPLE 2

1-[6'-(meta-chlorophenyl)pyridazin-3'-yl]-3-aminopyrazol-2-ene

A slurry of 3-chloro-6-(meta-chlorophenyl)pyridazine (10.25 g.) in anhydrous hydrazine (36 ml) was heated at 82° C. for 3 hours. Upon cooling a solid separated. The solid was isolated by filtration and recrystallized from ethanol to give 3-hydrazino-6-(meta-chlorophenyl)pyridazine, m.p. 173°–174°. When 3-hydrazino-6-(meta-chlorophenyl)-pyridazine was reacted with acrylonitrile using the same procedure described in Example 1, 1-[6'-(meta-chlorophenyl)-pyridazin-3'-yl]-3-aminopyrazol-2-ene was obtained, m.p. 196°–197° C.

EXAMPLE 3

When 3-chloro-6-(meta-tolyl)pyridazine and 3-chloro-6-(ortho-tolyl)pyridazine were reacted with hydrazine, using similar reaction conditions described in Example 2, 3-hydrazino-6-(meta-tolyl)pyridazine, m.p. 141°–142° C. and 3-hydrazino-6-(ortho-tolyl)pyridazine, m.p. 130°–131° C. were obtained respectively. These hydrazino compounds were reacted with acrylonitrile as described above, to give 1-[6'-(meta-tolyl)-pyridazin-3'-yl]-3-aminopyrazol-2-ene, m.p. 135°–136°

C., and 1-[6'-(ortho-tolyl)-pyridazin-3'-yl]-3-aminopyrazol-2-ene, m.p. 150°-151° C.

EXAMPLE 4

When the following hydrazino compounds were allowed to react with acrylonitrile as described in the procedure of Example 1, the following compounds were obtained:

| Pyridazinehydrazines | Products |
| --- | --- |
| 6-(ortho-chlorophenyl)-3-hydrazinopyridazine | 1-[6'-(ortho-chlorophenyl)-pyridazin-3'-yl]-3-aminopyrazol-2-ene; m.p. 165-166° C. |
| 6-(meta-chlorophenyl)-3-hydrazinopyridazine | 1-[6'-(meta-chlorophenyl)-pyridazin-3'-yl]-3-aminopyrazol-2-ene; m.p. 196-197° C. |
| 6-(para-chlorophenyl)-3-hydrazinopyridazine | 1-[6'-(para-chlorophenyl)-pyridazin-3'-yl]-3-amino pyrazol-2-ene; m.p. 278-279° C. |
| 6-(ortho-tolyl)-3-hydrazinopyridazine | 1-[6'-(ortho-tolyl)-pyridazin-3-aminopyrazol-2-ene; m.p. 150-151° C. |
| 6-(meta-tolyl)-3-hydrazinopyridazine | 1-[6'-meta-tolyl)-pyridazin-3'-yl]-3-aminopyrazol-2-ene; m.p. 135-136° C. |
| 6-(para-toly)-3-hydrazinopyridazine | 1-[6'-para-tolyl)-pyridazin-3'-yl]-3-aminopyrazol-2-ene; m.p. 249-250° C. |
| 6-methyl-3-hydrazinopyridazine | 1-[6'-methyl-pyridazin-3'-yl]-3-aminopyrazol-2-ene; m.p. 176-177° C. |
| 6-(para-acetamidophenyl)-3-hydrazinopyridazine | 1-[5'-para-acetamidophenyl)-pyridazin-3'-yl]-3-aminopyrazol-2-ene |
| 6-(meta-methoxyphenyl)-3-hydrazinopyridazine | 1-[6'-meta-methoxyphenyl)-pyridazin-3'-yl]-3-aminopyrazol-2-ene |
| 6-(para-benzyloxyphenyl)-hydrazinopyridazine | 1-[6'-(para-benzyloxyphenyl)-pyridazin-3'-yl]-3-aminopyrazol-2-ene |
| 6-(meta-cyanophenyl)-3-hydrazinopyridazine | 1-[6'-meta-cyanophenyl)-pyridazin-3'-yl]-3-aminopyrazol-2-ene |
| 6-(ortho,meta-dimethoxyphenyl)-3-hydrazinopyridazine | 1-[6'-(ortho-meta-dimethoxyphenyl)-pyridazin-3'-yl]-3-aminopyrazol-2-ene |
| 6-(para-dimethylaminophenyl)-3-hydrazinopyridazine | 1-[6'-(para-dimethylaminophenyl)-pyridazin-3'-yl]-3-aminopyrazol-2-ene |
| 6-(meta-fluoro-para-methoxyphenyl)-3-hydrazinopyridazine | 1-[6'-(meta-fluoro-para-methoxyphenyl)-pyridazin-3'-yl]-3-aminopyrazol-2-ene |
| 6-(meta-methyl-para-methoxyphenyl)-3-hydrazinopyridazine | 1-[6'-(meta-methyl-para-methoxyphenyl)-pyridazin-3'-yl]-3-aminopyrazol-2-ene |
| 6-(para-methylthiophenyl)-3-hydrazinopyridazine | 1-[6'-(para-methylthiophenyl)-pyridazin-3'-yl]-3-aminopyrazol-2-ene |
| 6-(para-phenoxyphenyl)-3-hydrazinopyridazine | 1-[6'-(para-phenoxyphenyl)-pyridazin-3'-yl]-3-aminopyrazol-2-ene |
| 6-(meta-trifluoromethylphenyl)-3-hydrazinopyridazine | 1-[6'(-meta-trifluoromethyl phenyl)-pyridazin-3'-yl]-3-aminopyrazol-2-ene |
| 6-methoxy-3-hydrazinopyridazine | 1-[6'-methoxy-pyridazin-3'-yl]-3-aminopyrazol-2-ene |
| 6-benzyl-3-hydrazinopyridazine | 1-[6'-benzyl-pyridazin-3'-yl]-3-aminopyrazol-2-ene |
| 5-methyl-3-hydrazinopyridazine | 1-[5'-methyl-pyridazin-3'-yl)-3-aminopyrazol-2-ene |
| 4-methyl-3-hydrazinopyridazine | 1-[4'-methyl-pyridazin-3'-yl]-3-aminopyrazol-2-ene |
| 3-hydrazinopyridazine | 1-(pyridazin-3'-yl)-3-aminopyrazol-2-ene |

EXAMPLE 5

When 6-phenyl-3-hydrazinopyridazine was reacted separately with methacrylonitrile and with crotonitrile using the procedure described in Example 1, 1-[6'-phenylpyridazin-3'-yl]-3-amino-4-methylpyrazol-2-ene, m.p. 205°-206° C., and 1-[6'-phenylpyridazin-3'-yl]-3-amino-5-methylpyrazol-2-ene, m.p. 210°-212° C., were obtained.

EXAMPLE 6

1-[6'-phenylpyridazin-3'-yl]-pyrazolidin-3-one or -[6'-phenylpyridazin-3'-yl]-3-hydroxypyrazol-2-ene It should be recognized that when x is hydroxy, the compound can exist in a tautomerism with its ketonic form (pyrazolidin-3-one). A slurry of 1-[6'-phenylpyridazin-3'-yl]-3-aminopyrazol-2-ene (10.5 g.) in 3N hydrochloric acid (150 ml.) was heated under reflux for 7 hours. The reaction was left to cool overnight. Filtration of the mixture gave 1-[6'-phenylpyridazin-3'-yl]-pyrazolidin-3-one hydrochloride as a yellow solid. This was crystallized from ethanol to give pure product, m.p. 245°-246° C.

The compounds of the present invention have anti-inflammatory activity and inhibitory effect against Type III hypersensitivity reaction. These compounds are useful for the therapy of rheumatoid arthritis, other inflammatory conditions, Type III hypersensitivity diseases and in diseases in which polymorphonuclear leukocytes accumulation contributes to the pathology.

The anti-inflammatory activity of these compounds was established by using a modification of the carrageenin pleurisy assay described by Vinegar et al. Proc. Soc. Exp. Biol. Med. 143:711 (1973). Table 1 shows the reduction in accumulation of exudate volume and leukocytes.

TABLE I

| Compound | Dose | % Inhibition | |
| --- | --- | --- | --- |
| | | Volume exudates | Cells |
| Phenylbutazone | 100 | 59 | 13 |
| 1-[6'-phenylpyridazin-3'-yl]-3-aminopyrazol-2-ene | 100 | 73 | 51 |

The ability of these compounds to inhibit Type III hypersensitivity reactions was demonstrated using the reverse passive Arthus assay as described by Carter and Krause Fed. Proc. 35, 774 (1976). Each compound was administered orally to a group of four animals.

The Arthus reaction represents one of the oldest and best studied models of immunological injury. It is produced by the injection of antigen locally into a hyperimmunized animal or by the injection of a small amount of antibody into the skin of an animal that has just previously been given a large amount of soluble antigen intravenously. In both cases the antigen and antibody become deposited in the walls of small venules. Plasma complement is rapidly bound and activated. Within a few hours neutrophils (PMNs) accumulate resulting in disruption of the basement membrane of vessel walls and marked edema and hemorrage in the surrounding tissue.

Although the etiology of rheumatoid arthritis remains obscure, it is almost certain that immunological mechanisms play an important role in the pathogenesis of this disease. Therefore, inflammation induced by immunological reactions, which are believed to be important in the inflammatory processes of rheumatoid arthritis, make particularly desirable tools for the screening of potential anti-inflammatory agents. The usefulness of such a model depends upon how closely it represents the underlying pathological mechanisms of rheumatoid arthritis.

Based upon currently available evidence, a plausible sequence of events leading to the joint leisions in rheumatoid arthritis can be constructed. An initiating antigen, perhaps a transient synovial infection, results in an immune response and retention of the antigen within the joint structure. The interaction of antigen with developing antibodies results in the deposition of immune complexes. These complexes may fix and activate complement, causing the generation of a number of phlogistic and chemotactic substances. Phagocytosis of the complexes by attracted polymorphonuclear leukocytes (PMNs) leads to the release of lysosomal constituents. The enzymes released from lysosomes can erode articular cartilage and produce inflammation in the joint. The striking resemblance of these events to the Arthus phenomenon point to the utility of the Arthus reaction as a screen for anti-inflammatory compounds.

The reverse passive Arthus reaction test in rats is conducted as follows: Male Sprague-Dawley rats weighing approximately 130–160 g. are used, 4 rats per group. All animals are injected intravenously with 0.5 ml. 0.075% Bovine Serum Albumin (B.S.A.)+2% Evans Blue solution. Each rat then receives an oral dose of drug; one drug is administered per group.

Thirty minutes subsequent to drug dosing, each animal is injected intradermally with 0.05 ml. 1.44% Anti-B.S.A. into the dorsal skin. Four hours later the animals are sacrificed, the dorsal skin reflexed, and the lesion excised. Two perpendicular diameters of each lesion are measured. The average diameters of the lesions from the treated groups are compared with the average diameters from the control group to determine any drug effect.

Table II shows the percentage of reduction in lesion area produced by several representative compounds.

TABLE II

| Compound | Dose mg/kg | % Inhibition of lesion of dermal Arthus reaction |
| --- | --- | --- |
| Phenylbutazone | 100 | inactive |
| 1-[6'-phenylpyridazin-3'-yl]-3-amino-pyrazol-2-ene | 100 | 65 |
| 1-[6'-(meta-chloro-phenylpyridazin-3'-yl]-3-aminopyrazol-2-ene | 100 | 51 |
| 1-[6'-ortho-chlorophenyl-pyridazin-3'-yl]-3-amino-pyrazol-2-ene | 100 | 58 |
| 1-[6'-phenyl-pyridazin-3'-yl]-3-amino-5-methylpyrazol-2-ene | 100 | 54 |

What is claimed is:

1. A compound of the formula

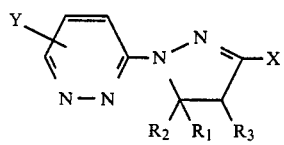

wherein $R_1$, $R_2$ and $R_3$ independently of one another denote hydrogen or loweralkyl, X is hydroxy or amino, and Y is

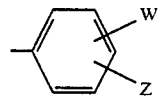

wherein W and Z independently of one another denote hydrogen, halo, loweralkyl, loweralkoxy, trifluoromethyl, acetamido, cyano, diloweralkylamino, phenoxy and loweralkylmercapto, and pharmaceutically acceptable salts thereof.

2. A compound of claim 1 wherein $R_1$ and $R_2$ are hydrogen, $R_3$ is hydrogen or loweralkyl, Y is

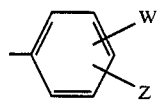

wherein W and Z independently of one another denote hydrogen, halo or loweralkyl.

3. A compound of claim 2 wherein Y is

wherein W is hydrogen and Z is hydrogen, halo or loweralkyl.

4. A compound of claim 3 wherein $R_3$ is methyl, $R_1$ and $R_2$ are hydrogen, and Y is

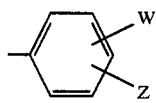

wherein W and Z are hydrogen, chloro or methyl.

5. A compound of claim 4 wherein X is hydroxy.

6. A compound of claim 1 wherein $R_1$ and $R_2$ are methyl, $R_3$ is hydrogen, Y is

wherein W is hydrogen and Z is hydrogen, chloro or methyl.

7. A pharmaceutical composition useful for the treatment of inflammatory conditions which comprises a compound of the formula

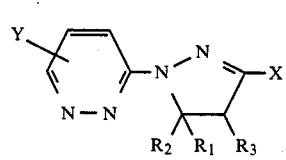

wherein $R_1$, $R_2$ and $R_3$ independently of one another denote hydrogen or loweralkyl, X is hydroxy or amino, and Y is

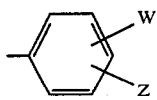

wherein W and Z independently of one another denote hydrogen, halo, loweralkyl, loweralkoxy, trifluoromethyl, acetamido, cyano, diloweralkylamino, phenoxy and loweralkylmercapto, and pharmaceutically acceptable salts thereof, and a pharmaceutically acceptable carrier.

8. The composition of claim 7 wherein $R_1$ and $R_2$ are hydrogen, $R_3$ is hydrogen or loweralkyl, Y is

wherein W and Z independently of one another denote hydrogen, halo or loweralkyl.

9. The composition of claim 8 wherein Y is

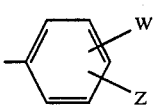

wherein W is hydrogen and Z is hydrogen, halo or loweralkyl.

10. The composition of claim 9 wherein $R_3$ is methyl, $R_1$ and $R_2$ are hydrogen, and Y is

wherein W and Z are hydrogen, chloro or methyl.

11. The composition of claim 10 wherein X is hydroxy.

12. The composition of claim 7 wherein $R_1$ and $R_2$ are methyl, $R_3$ is hydrogen, Y is

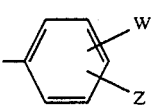

wherein X is hydrogen and Z is hydrogen, chloro or methyl.

13. A method of treating or relieving the symptoms associated with inflammation comprising administering to a patient in need of such treatment a therapeutically effective amount of an anti-inflammatory agent of the formula

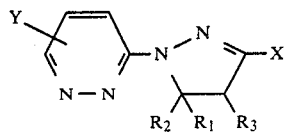

wherein $R_1$, $R_2$ and $R_3$ independently of one another denote hydrogen or loweralkyl, X is hydroxy or amino, and Y is

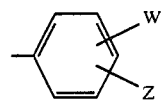

wherein W and Z independently of one another denote hydrogen, halo, loweralkyl, loweralkoxy, trifluoromethyl, acetamido, cyano, diloweralkylamino, phenoxy or loweralkylmercapto and pharmaceutically acceptable salts thereof.

14. The method of claim 13 wherein $R_1$ and $R_2$ are hydrogen, $R_3$ is hydrogen or loweralkyl, Y is

wherein W and Z independently of one another denote hydrogen, halo or loweralkyl.

15. The method of claim 14 wherein Y is

wherein W is hydrogen and Z is hydrogen, halo or loweralkyl.

16. The method of claim 15 wherein $R_3$ is methyl, $R_1$ and $R_2$ are hydrogen, and Y is

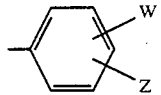

wherein W and Z are hydrogen, chloro or methyl.

17. The method of claim 16 wherein X is hydroxy.

18. The method of claim 13 wherein $R_1$ and $R_2$ are methyl, $R_3$ is hydrogen, Y is

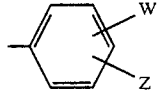

wherein W is hydrogen and Z is hydrogen, chloro or methyl.

* * * * *